United States Patent
Taylor

(10) Patent No.: US 6,406,725 B1
(45) Date of Patent: Jun. 18, 2002

(54) METHOD OF VISUALLY LABELLING AGRICULTURAL COMMODITES

(76) Inventor: Roy D. Taylor, 3805 Vardon Ct., Woodridge, IL (US) 60517

( * ) Notice: Subject to any disclaimer, the term of this patent is extended or adjusted under 35 U.S.C. 154(b) by 1 day.

(21) Appl. No.: 09/758,700

(22) Filed: Jan. 11, 2001

(51) Int. Cl.$^7$ .......................... C01N 33/02; C01N 21/29
(52) U.S. Cl. ..................... 426/87; 426/132; 426/250; 426/549; 426/615; 426/629
(58) Field of Search .................. 426/87, 132, 250, 426/549, 615, 629

(56) References Cited

U.S. PATENT DOCUMENTS

| | | | | |
|---|---|---|---|---|
| 2,685,517 A | * | 8/1954 | Dunmire ........................ 99/11 |
| 2,868,644 A | * | 1/1959 | Eisenberg ....................... 99/2 |
| 3,438,781 A | * | 4/1969 | MacMillan et al. .............. 99/2 |
| 4,029,820 A | * | 6/1977 | Eisenberg ..................... 426/74 |
| 4,188,408 A | * | 2/1980 | Eisenberg ..................... 426/74 |
| 4,654,165 A | * | 3/1987 | Eisenberg ................ 252/408.1 |
| 4,840,909 A | * | 6/1989 | Rossoff ....................... 436/20 |
| 5,397,834 A | | 3/1995 | Jane et al. .................. 525/54.1 |
| 5,523,293 A | | 6/1996 | Jane et al. ..................... 514/21 |
| 5,710,190 A | | 1/1998 | Jane et al. .................. 521/102 |
| 6,200,610 B1 | * | 3/2001 | Graham ....................... 426/87 |

FOREIGN PATENT DOCUMENTS

DE 19749221 * 5/1999

OTHER PUBLICATIONS

Wakeman, Res. Information Note, Forestry Commission, U.K., No. 6, pp. 2, 1975.*

* cited by examiner

Primary Examiner—Chhaya D. Sayala
(74) Attorney, Agent, or Firm—Bullwinkel Partners, Ltd.

(57) ABSTRACT

A method of visually marking an agricultural commodity before or after processing is provided. The markers are colored plant protein-derived pellets that can be made in different sizes and shapes for mixing into various agricultural commodities as a visual label or "taggant" during storage and shipment. The invention greatly simplifies the tracking and identification of commodity products in storage or in transit.

13 Claims, No Drawings

METHOD OF VISUALLY LABELLING AGRICULTURAL COMMODITES

BACKGROUND

1. Field of the Invention

This patent relates to a method for visually identifying agricultural commodities and processed commodities. Specifically, this patent relates to labeling agricultural commodities with biodegradable marker pellets, as well as labeling dry ingredients made from processed commodities to be used for human foods and animal feeds.

2. Description of the Related Art

Some consumers and consumer organizations have expressed reservations about the introduction of genetically modified organisms (GMO) directly into human foods or indirectly via animal feeds. These groups have pushed for more stringent food labeling requirements with the stated concern of protecting the individual's freedom to choose to buy, or not to buy, food products containing or derived from "GMO" ingredients. The entire grain industry is now being pressured to segregate and label GMO-containing commodity shipments, as well as food and animal feed products and ingredients made from those commodities.

Certain major markets, notably the European Union, have put into place domestic food labeling regulations that can only be complied with if "GMO" ingredients are segregated and labeled. This, in turn, has led to commodity buyers adding tender specifications requiring certification of GMO content and/or certification that shipments do not contain any transgenic varieties not registered in the importing country.

Large quantities of agricultural commodities are already marketed under the designation "identity-preserved" (IP) and are essentially segregated from the time they leave the farm until arrival at the end-use processors. Most IP shipments have historically been containerized, providing physical isolation of the material to supplement paper certifications of origin identity. However, as demand for IP commodities has grown along with requests or requirements to certify GMO content and varietal registration status, it has become physically impossible to bag or containerize all IP shipments.

Two of the greatest challenges facing the grain industry, therefore, are to (1) find a credible way to segregate and label IP bulk commodity shipments; and (2) find a credible way to keep U.S. approved but not yet foreign registered varieties out of the export market. Any response to these challenges must address the core issue of how to easily and simply distinguish between different varieties that are visually indistinguishable.

The technology for testing for the presence of specific individual genetic traits or certain proteins is rapidly evolving and being used by buyers and sellers alike. Unfortunately, testing cannot prevent accidental, or intentional, commingling of shipments at grain elevators or export terminals.

Known methods for marking commodity products include (a) using paper confetti taggants (strips of paper with information printed on them) mixed into grains at the grain elevator, and (b) using various dyes. However, neither of these methods are used much, if at all. Once added, paper confetti cannot be removed from a commodity, and it creates a fire hazard when the marked commodity is processed with certain types of commonly used equipment, such as hammer mills. Dyes also cannot be removed once they are applied, and they can result in unnaturally colored products made from the dyed commodity.

Thus it is an object of the present invention to provide a practical, cost effective method of physically marking or labeling bulk shipments to identify IP commodities in bulk.

Another object of the invention is to provide a method for marking bulk shipments that is safe from a health and environmental standpoint.

Still another object of the invention is to provide a method for marking bulk commodity shipments that does not interfere with routine processing of the commodity.

Yet another object of the invention is to provide a means for marking bulk commodity shipments that cannot be easily removed in transit.

Yet another object of the invention is to provide a means for marking bulk commodity shipments that cannot be easily counterfeited.

Yet another object of the invention is to provide a method for marking commodities after they have been processed into other products, such as ingredients for human foods and animal feeds.

Further and additional objects will appear from the description and appended claims.

SUMMARY OF THE INVENTION

The present invention is a method of visually marking an agricultural commodity before or after processing. The markers are plant protein-derived pellets, such as soy-derived pellets, that can be made in different sizes and shapes for mixing into various agricultural commodities and commodity products as a visual label or "taggant" during storage and shipment. The invention greatly simplifies the tracking and identification of commodities and commodity products in storage or in transit.

DETAILED DESCRIPTION OF THE INVENTION

The present invention is an environment friendly method of visually labeling commodities and commodity products using colored plant protein-derived pellets. The invention may be used to track commodities in storage or in transit. Potential uses of the invention include labeling agricultural commodities at the point of origin (eg. on the farm or at the grain elevator) and labeling commodities after any type of testing or certification process. Commodities that may be marked according to the method disclosed herein include soybeans, barley and corn, although the method may be used to mark any suitable agricultural commodity or processed commodity.

The method may be practiced as follows. At whatever point in the distribution system a given commodity shipment has its identity certified (e.g., "GMO"/"GMO-free", certified seed, organically grown, non-EU registered, etc.) one or more of the organizations that supervise commodity testing and certifications could also supervise the tightly controlled addition of a specific, low level concentration of color-coded marker pellets. It then becomes simple to visually confirm the presence of these markers at subsequent points during shipment or at destination.

At the low inclusion rate foreseen, pellets the approximate size and density of the commodity grain or bean to be marked may be used. The pellets would not be screened out, but would be processed along with the commodity with no noticeable affect on the quality of end products.

Where desired, the pellets could also be made larger than the size of the bean or grain, allowing them to be removed at the shipment destination with a simple screening operation.

Marker pellets may be used to label shipments between farms and the initial designated elevator or collection point. This type of marking could be especially important where more than one variety is being handled at the same collection point.

Marker pellets also may be used to label certain types of dry processed commodity products in cases where it is necessary or desirable to segregate the processed product from other visually similar products.

Manufacturing the Marker Pellets

A manufacturing process for producing plant protein-derived colored pellets has been developed. No special equipment is required for the manufacturing process. The pellets may be produced from readily available ingredients. One of the many possible compositions of the pellets is provided in Table 1 below. All of the ingredients in Table 1 are GRAS (Generally Recognized as Safe). These plant protein-derived plastic pellets can be made in various colors and easily incorporated into bulk commodity shipments as a visual marker or taggant.

TABLE 1

Composition of Marker Pellets
(Measurements based on 100 parts soy protein and starch)

| Soy protein isolate | 70% dry weight |
| --- | --- |
| Starch | 30% dry weight |
| Glycerol | 13 parts |
| Water | 13 parts |
| Potassium sorbate | 1 part |
| Sodium tri-polyphosphate | 3 parts |
| Sodium sulfite | 0.35 parts |
| Dye (red) | 0.10 parts |

The soy pellets of Table 1 were made in the following manner. Sodium sulfite was dissolved in water and then glycerol was added to the solution. Soy protein, starch, potassium sorbate, sodium tri-polyphosphate and red dye were mixed together in a mixer. After about two minutes, the solution containing sodium sulfite, water and glycerol was added to the premix in the mixer. Mixing continued for thirty minutes.

The premix was fed to an extruder at a rate of 6 lb/hr using a twin-screw feeder with a die temperature of 118 degrees Centigrade. The strands exiting the extruder were red and clear. The strands were readily pelletized to provide red colored marker pellets.

Adding the Marker Pellets to the Commodity

The commodity may be any suitable agricultural commodity, such as soybeans, corn, oats or barley, or any suitable processed commodity. For convenience, the use of the term "grain" in the specification and the claims that follow shall refer to all suitable agricultural commodities and processed commodities, unless otherwise stated.

For both large and small pellets, one easy method of adding the marker pellets to the grain is to simply pour a pre-determined quantity of markers (e.g., from 2×2 gallon pails) under or on top of each hopper load of grain dumped into the truck on the farm, or on top of each truckload as it passes from pit to bin at the collection point. The markers will be quite homogeneously mixed by the natural vortexes that occur during the dumping process, including the discharge of the bins into rail cars.

The marker pellets could also be added to the grain on farm by augering them on top of the last load going into a particular silo. The silo could be sealed until it is time to transfer the commodity. When the grain is augered from the silo into a truck for delivery, the natural central vortex that occurs mixes in the pellets.

Alternatively, specially designed metering devices could be used to measure a controlled amount of pellets during large volume transfers of grain. A leading manufacturer of such equipment has confirmed the technical feasibility of this type of measuring.

The appropriate concentration of marker pellets in the grain depends in part on whether the sole objective of adding the marker pellets is to visually tag the material. If so, the rate of addition may be about 0.5% by weight (5 kg per metric ton), but could be as high as 2.0% by weight.

One or more designated agents may be authorized to supervise and control distribution and addition of the marker pellets. These designated agents may be county agents, agents of organic certifying organizations, agents of state crop improvement associations, independent crop consultants, etc., and in some cases agents of "IP"/specialty crop buyers. When notified of the scheduled harvest of designated IP fields (certified seed, EU registered/not registered, organically grown, etc.), the local certifying agent could supervise or direct the allocation of the appropriate quantity and color of markers to individual farms.

Use of Markers to Indicate Presence of Commingling

On arrival at the collection point or at a processor, the first level of control for possible commingling is checking whether the marker pellets are appearing at an expected rate as the truck is unloaded. The easily visible markers make it significantly more difficult to accidentally direct the load into the wrong bin.

While accidental or intentional adulteration of a shipment cannot be physically prevented, the use of the marker pellets will make it much easier to detect and isolate "contaminated" or diluted shipments before or during consolidation with other shipments.

Removal of the Marker Pellets from the Grains

The large version of the pellets can be screened out when the grain is unloaded at the point of destination. The small version of the pellets, which are about the same size as the agricultural commodity, need not be removed from the agricultural commodity destined for animal feeds or feed ingredients because they are biodegradable and harmless to livestock.

Disposal of Marker Pellets

Disposal of spilled pellets, leftover inventory or screened-out large pellets, is not a problem. One of the attractive aspects of this method is that while the useful life of the soy-based pellets is more than adequate for the envisaged marking purposes, the pellets are easily and safely disposed of by composting or burial.

Prevention of Counterfeiting

The marker pellets themselves can be marked in such a way that allows definitive identification of authentic markers in the field. This technology is commercially available and is currently used in variety of food products. If counterfeit pellets are suspected, a simple test can be conducted in a matter of minutes that can definitively confirm the authenticity of the marker pellets.

Other modifications and alternative embodiments of the invention are contemplated which do not depart from the spirit and scope of the invention as defined by the foregoing teachings and appended claims. It is intended that the claims cover all such modifications that fall within their scope.

What is claimed is:

1. A method of visually labeling an agricultural commodity comprising the steps of:

(a) providing a quantity of plant protein-derived marker pellets that are visually discernable from the agricultural commodity;

(b) adding a desired amount of the marker pellets to the agricultural commodity.

2. The method of claim 1 wherein the pellets are approximately the same size as the agricultural commodity.

3. The method of claim 1 wherein the pellets are larger than the agricultural commodity.

4. The method of claim 1 wherein the pellets comprise soy protein and starch.

5. The method of claim 4 wherein the pellets comprise about 70% dry weight soy protein and about 30% dry weight starch.

6. The method of claim 5 wherein the pellets are formed by extrusion.

7. The method of claim 1 wherein the pellets are added to the agricultural commodity by pouring the pellets on top of the agricultural commodity.

8. The method of claim 1 wherein the pellets are added to the agricultural commodity by augering the pellets on top of the agricultural commodity.

9. The method of claim 1 wherein about 0.5% by weight marker pellets are added to the agricultural commodity.

10. The method of claim 1 comprising the further step of checking the concentration of marker pellets with a densitometer.

11. The method of claim 3 further comprising the step of removing the pellets from the agricultural commodity after the need for visual labeling is over.

12. The method of claim 11 wherein the pellets are removed by screening.

13. The method of claim 1 wherein the pellets are themselves marked to prevent counterfeiting.

* * * * *